United States Patent [19]

Coleman et al.

[11] Patent Number: 4,518,595
[45] Date of Patent: May 21, 1985

[54] METHOD FOR TREATING DIABETES USING DHEA COMPOUNDS

[75] Inventors: Douglas L. Coleman, Seal Harbor, Me.; Norman Applezweig, New York, N.Y.; Edward H. Leiter, Otter Creek, Me.

[73] Assignee: The Jackson Laboratory, Bar Harbor, Me.

[21] Appl. No.: 515,354

[22] Filed: Jul. 19, 1983

[51] Int. Cl.³ .............................................. A61K 31/56
[52] U.S. Cl. .................................... 514/178; 514/866
[58] Field of Search .......................... 428/243; 424/243

[56] References Cited

PUBLICATIONS

Coleman et al., "Diabetes", vol. 31, Sep. 1982, pp. 830-833.

Primary Examiner—Elbert L. Roberts
Attorney, Agent, or Firm—Daniel H. Kane, Jr.

[57] ABSTRACT

Diabetes is treated by orally administering a dehydroepiandrosterone (DHEA) compound selected from the group consisting of DHEA, DHEA sulfate and soluble DHEA compounds. The DHEA compound is preferably administered in finely dispersed form, powdered or solution, mixed with the food diet of the diabetic in a dosage range of up to 0.4% by weight of the food diet. The pharmacological activity and utility of DHEA as a potent anti-diabetic agent and anti-hyperglycemic agent over a variable range of genetic background is documented.

20 Claims, 3 Drawing Figures

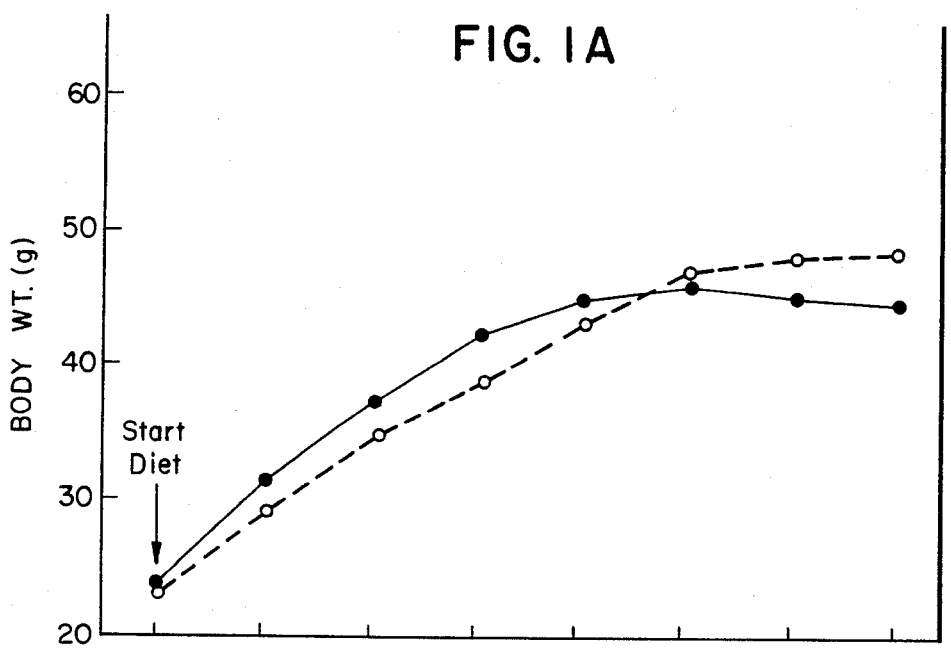
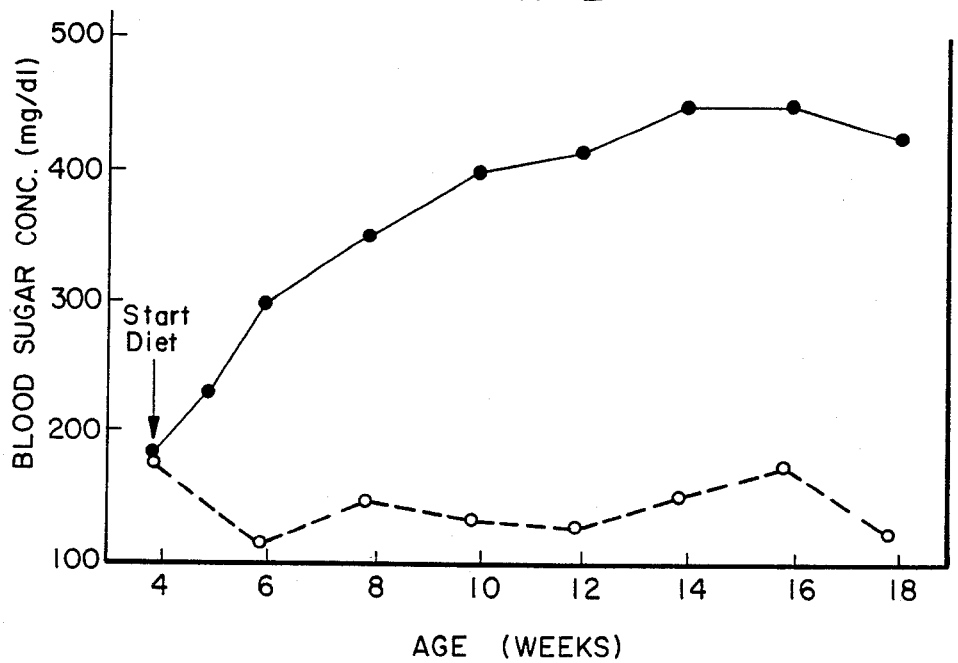

METHOD FOR TREATING DIABETES USING DHEA COMPOUNDS

TECHNICAL FIELD

This invention relates to a new method for treating diabetes and for enhancing the function of pancreatic β-cells of the islets of Langerhans.

BACKGROUND ART

Dehydroepiandrosterone (DHEA) and its sulfate derivative are major adrenal secretory products in humans, yet no biological function for DHEA has been definitely established. Decreased secretion of DHEA has been associated with advancing age in both sexes, and with certain types of breast cancer in women. Chronic treatment with DHEA in the diet has been shown to increase longevity in rodents by retarding the development of specific diseases associated with particular strains or mutants. Thus, ameliorative biological effects have been established relating to obesity, tumor development, aging, and immune function. The steroid DHEA appears to have many of the beneficial effects of caloric restriction without actually decreasing the amount of food eaten. Popular articles have appeared documenting the interest in DHEA as a potential weapon against obesity, cancer and the aging process, for example, Rosenfeld, "The Re-examination of a Curious Hormone", Science 81, 20 and 24 (November, 1981), and Rosenfeld, "Superpowder", Omni, 59, 60, 110 and 112 (August, 1982). However, prior to the work of the present inventors, no one has ever found or established a beneficial effect of DHEA as an anti-diabetic or anti-hyperglycemic agent. In fact, certain studies reported no correlation with blood sugar. The full correct chemical name for DHEA is androst-5-ene-3β-ol-17-one.

British Patent Specification No. 1,246,639 describes the manufacture and use of dehydroepiandrosterone esters for the treatment of menopause and symptoms and complaints associated with menopause, without androgenic side effects or virilisation phenomena. The ester is formed, for example, by reacting the DHEA with an acid such as an acid anhydride or acid halide in the presence of pyridine. U.S. Pat. No. 3,963,707 describes a variety of steroid compounds having anti-tumor activity. The patent describes methods for preparation of such compounds for inhibiting the growth of tumors. Among the steroid hormones mentioned for use in the compound preparation described in this patent is DHEA. U.S. Pat. No. 4,042,459 is of only related interest and describes the use of microbial transformation to selectively degrade steroids including DHEA. No references prior to the inventors' own work has suggested, discovered, established or found a utility for DHEA in the treatment of diabetes.

OBJECTS OF THE INVENTION

It is therefore an object of the present invention to provide a new method for treating diabetes and enhancing the function of pancreatic islet β-cells using the inventor's documented discovery of the utility of DHEA as a potent oral anti-diabetic agent and a potent oral anti-hyperglycemic agent.

Another object of the invention is to provide new methods of administering DHEA for the effective treatment of diabetes, for regeneration or enhancement of the islets of Langerhans in diabetics, and perhaps for decreasing insulin resistance.

DISCLOSURE OF THE INVENTION

In order to accomplish these results the present invention provides a new method for treating diabetes and enhancing the function of β-cells in the islets of Langerhans of the pancreas of diabetics by orally administering DHEA and soluble DHEA compounds. According to the invention DHEA or its soluble compounds are administered in a finely dispersed form, for example, in a finely dispersed powder or solution typically mixed with the food diet. The full beneficial effects of the DHEA treatment are achieved by dosages of DHEA compound in a range of up to 0.4% by weight of the food diet of the diabetic. Beneficial effects have been documented with dosage concentrations in the range, for example, of 120 mg to 480 mg per day per kg body weight.

According to a preferred example, the DHEA compound selected from the group consisting of DHEA, DHEA sulfate, and soluble DHEA compounds is rendered in finely dispersed form, either a finely dispersed powder or solution and is thoroughly mixed with the food diet in the beneficial range of percent by weight dosage.

In the case of DHEA itself, the compound is dissolved in a DHEA solvent such as acetone or other ketone for dispersion of the molecules. The DHEA compound solution is then mixed with the food diet followed by evaporation of the solvent prior to ingestion. Evaporation of the acetone effectively leaves the DHEA in a finely dispersed powdered form thoroughly mixed through the food diet for more effective assimilation into the mammalian system.

In the case of DHEA sulfate which is soluble in water, the DHEA sulfate solution may be mixed with the food diet without concern over complete evaporation of the aqueous solvent prior to ingestion. The invention also contemplates the application and effectiveness of other soluble DHEA compounds such as DHEA glucuronide.

A feature and advantage of the invention is that administering a food diet supplemented by DHEA compound in a percentage by weight in a range of up to 0.4% restores hyperglycemia to normal and improves glucose tolerance even in severely diabetic mammals. For example, workers at The Jackson Laboratory of Bar Harbor, Maine, have identified two mutant genes, the obese (ob) and diabetes (db) genes which produce diabetic conditions and conditions of obesity in mice. The severity of the diabetes depends on background genetic factors inherent in the inbred strains in which the mutations are maintained and expressed. Typical mouse strains in which the diabetes and obesity genes are maintained are The Jackson Laboratory C57BL/KsJ mice, referred to more briefly as the BL/Ks mice or Black Kaliss, and the C57BL/6J mice, referred to more briefly as the BL/6 or Black Six mice. In the BL/Ks mice the obese (ob) mutation and the diabetes (db) mutation elicit an exaggerated obesity and a severe life shortening diabetes. This diabetes is characterized by hyperplasia and hypertrophy of the beta cells of the islets of Langerhans followed by severe degeneration and atrophy of the islets, rising blood glucose concentrations over 400 mg/dl, and death at 5–8 months. In the BL/6 genetic background mice both mutations produce severe obesity but with a transient well-compensated diabetes.

According to the findings of the present invention, the method of treating diabetes by administering DHEA compounds does not substantially effect the degree of obesity or food consumption. On the other hand, the most striking effect of DHEA treatment according to the method is almost total prevention of the severe atrophy and degeneration of the islets of Langerhans typical of the diabetes syndrome in BL/Ks mutants. DHEA treatment converts the severe diabetes to a well-compensated diabetes despite severe obesity and residual insulin resistance.

The example embodiments hereafter set forth confirm the finding of the invention that DHEA is a potent anti-hyperglycemic and anti-diabetic agent when fed to mammals with inherited obesity and glucose intolerance syndromes. Further, improved glucose tolerance is observed in even very old animals treated with DHEA for 4 weeks compared with untreated, aged animals.

A critical finding of the present invention is that the utility of DHEA compounds as potent anti-diabetic and anti-hyperglycemic agents is not dependent upon the genetic background of the animal strain. Thus, the improvements in glucose tolerance in host animals maintaining the diabetes and obesity mutations as a result of orally administering DHEA were not dependent upon inbred strain background whether BL/Ks or BL/6. On the other hand, anti-obesity and anorectic effects of the DHEA steriod compound were dependent upon the genetic background of the inbred strain and were only effective, for example, in the BL/6 mice. This independence of the effectiveness of DHEA from genetic background and its effectiveness over a range of genetic background provides justification for inferring its potency for treatment of diabetes and enhancing $\beta$-cell function in a wide variety of mammals including humans.

Another advantage of the method of the invention is that the test animals show no apparent adverse effects to DHEA treatment. The effects of DHEA, while beneficial, are fully reversible by cessation of administration of the compound. Furthermore, intervention with DHEA treatment according to the present method may take place at any stage of the diabetic cycle. The diabetic cycle may be typically characterized by hyperactivity of the pancreas and hyperinsulinism followed by degeneration and then atrophy of the $\beta$-cells of islets of Langerhans. Intervention at the early stages according to the method can actually avert the stages of degeneration and atrophy maintaining the islets in healthy condition despite continuing hyperactivity. Intervention at the later states can actually reverse the process resulting in regeneration and enhancement of $\beta$-cell function. Furthermore, these beneficial effects have been found according to the invention to be independent of the genetic background of the inbred strain of the animal apparently responding specifically to the diabetes producing mutations whatever the host.

While some modulation of the effectiveness of DHEA by the genetic background of the host is suggested by the findings and to be expected, this does not rise to the marked variation in the severity of the diabetes-obesity syndrome itself which results from expression of the mutations in different genetic strains.

Further background on the animal models which have demonstrated the utility of the present invention can be found in the article by Douglas L. Coleman, "Diabetes-Obesity Syndromes in Mice", 31 *Diabetes*, 1–6 (April 1982). The work of the present invention and demonstration of its utility is further set forth in the articles Coleman et al, "Therapeutic Effects of Dehydroepiandrosterone (DHEA) in Diabetic Mice", 31 *Diabetes*, 830–833 (September 1982), and Coleman et al, "Effect of Genetic Background on the Therapeutic Effects of Dehydroepiandrosterone (DHEA) in Diabetes-Obesity Mutants in Mice", accepted for publication in the journal *Diabetes* for the December 1983 or January 1984 issue, a copy of which article accompanies this patent application for the file history. It is theorized that the DHEA compound is operative as a potent anti-diabetic agent through a number of possible pathways including pharmacological activity decreasing insulin resistance associated with advanced age, increasing glucose metabolism or clearance, improving intestinal absorption of nutrients, especially carbohydrates, and immunosuppression of documented autoimmunity against $\beta$-cells and islets.

Other objects, features and advantages will become apparent in the following specification and accompanying examples.

BRIEF DESCRIPTION OF THE DRAWINGS

FIG. 1A is a graph of the effect of treatment according to the invention on weight gain in BL/Ks diabetes mice based upon data compiled from 8 male mice per group. The solid line indicates data for mice fed on plain chow while the dash line connects data for mice on a food diet of 0.4% by weight DHEA.

FIG. 1B is a graph showing the effect of treatment according to the present invention on blood sugar concentrations in BL/Ks diabetes mice. The solid line connects data for mice fed on plain chow while the dash line connects data for mice on a food diet 0.4% by weight DHEA. The cross hatched region represents the normal range of blood sugar concentration.

DETAILED DESCRIPTION OF PREFERRED EXAMPLES AND BEST MODE OF THE INVENTION

Material and Methods

Figure 2A:
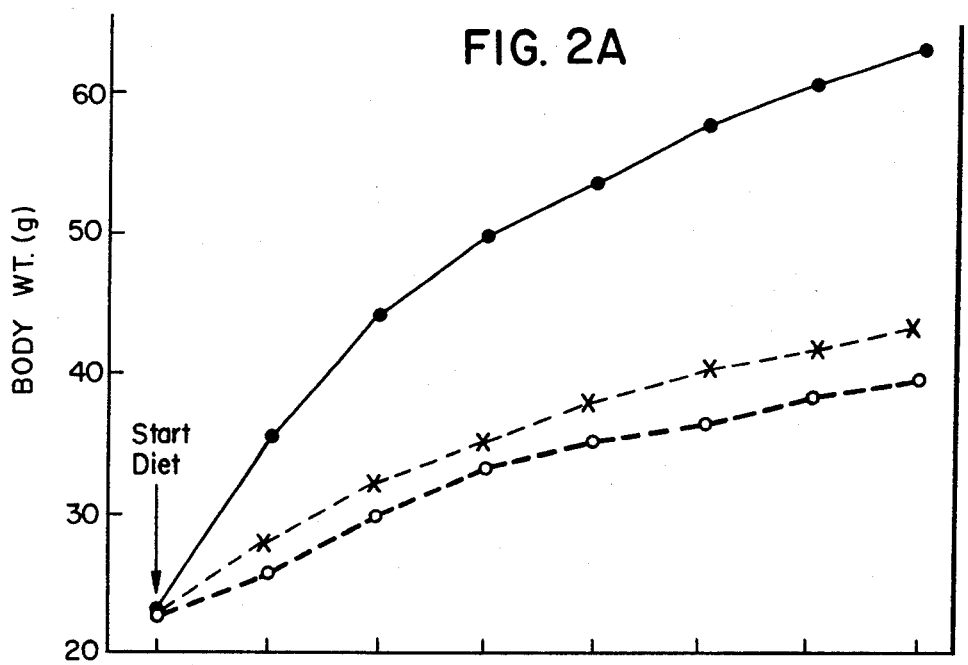
FIG. 2A is a graph showing the effect of treatment according to the invention on weight gain in BL/6 diabetes mice based on data compiled from 8 male mice per group. The solid line connects data for mice fed on plain chow. The light dash line connects data point x's for mice fed a food diet supplemented 0.1% by weight DHEA. The heavy dash line connects data point 0's for mice on a food diet supplemented 0.4% by weight DHEA.

Diabetes (db/db) and normal (+/+) control mice of the BL/6 strain and obese (ob/ob) mice of the BL/Ks strain were produced in the research colony of The Jackson Laboratory, Bar Harbor, Me. 04609. Obese (ob/ob) mice of the BL/6 strain were obtained from the Animal Resources Division of The Jackson Laboratory. Male mice were used in most studies except where indicated otherwise. The aged mice, two groups of 12 BL/6 female mice aged 1 and 2 years respectively, were obtained from the research colony of Dr. David E. Harrison of The Jackson Laboratory.

To test the efficacy of DHEA on pre-weaning mutant mice prior to development of any symptoms of diabetes or obesity, BL/Ks or BL/6 misty diabetes mice (m db/m db) were used for ease of identification of future diabetic mice. Such mice have the coat color misty (m) and diabetes (db) genes coupled on the same chromosome so that the future diabetic mice have a distinctive grey pelage coat color. The development of these congenic strains has been described in Coleman, D. L., "Hyperinsulinemia in Preweaning Diabetes Mice". 10 *Diabetologia*, 607–610 (1974). The introduction of the misty (m) gene does not affect the development of the diabetes syndrome in either strain. In these studies, heterozygous breeding pairs were fed chow containing 0.4% DHEA to provide maximum exposure of the developing fetuses to DHEA and to permit access by the mouse pups only to DHEA-containing diet through the time of spontaneous weaning.

In each study, pre-weanling, weanling, or aged mice, were divided into groups, one fed plain chow alone and others fed powdered chow into which DHEA had been incorporated as heretofore described. The DHEA was substantially pure (>99% purity androst-5-ene-3β-ol-17-one in finely dispersed powdered form. The powdered diets were fed in food cups that were filled every second day. In food consumption studies, the powdered chow containing DHEA was re-pelleted in a hydraulic press (5000 pounds/sq. in.) and weighed amounts of these pellets were fed each day. Daily food consumption was determined by weighing the amount left after 24 hr. Old Guilford 96 (trademark) chow was used for the food diet.

Mice were weighed weekly at the time of bleeding for determination of the blood sugar concentration. Plasma immunoreactive insulin (IRI) concentrations were determined periodically during the treatment period and at the time of termination of each experiment. After killing, the pancreas was removed, weighed, and one half was fixed in Bouin's solution for subsequent histological study and morphological analysis and the other half homogenized in acid-ethanol (1.5% concentrated HCl in 70% ethanol) to determine pancreatic insulin content. Blood glucose concentration, (B.S.) insulin concentration and glucose tolerance tests were carried out as previously described in Coleman, D. L., and Hummel, K. P., "Studies with the Mutation Diabetes in the Mouse", 3 *Diabetologia*, 238–248 (1967). The islet area and percent of granulated beta cells were measured using a Optomax (trademark) image analyzer system manufactured by Optomax, Hollis, N.H. Hydrated 5 m sections of Bouin's fixed tissues were stained with aldehyde fuchsin to detect beta cells. Islets for measurement were selected at random until data from 8–15 individual islets were accumulated per mouse. These were averaged to give an average value for islet area and percent of granulated beta cells. Data are expressed as mean ±SEM (Standard Error of the Mean) for the individual means of mice from various treatment groups. Statistical comparisons were calculated using the Student's "t" test. Differences were considered significant at $p<0.01$.

Results for Post-Weaning Diet Treatment

Diabetes (db) mutants maintained in the BL/Ks strain inbred background and fed a diet 0.4% by weight DHEA (dashed line) gained weight at a rate not significantly different than those mutants fed plain chow (solid line) as shown in FIG. 1A. The food consumption did not change in BL/Ks mutants fed 0.4% by weight DHEA. Changes in average blood sugar concentrations of mutants fed plain chow alone (solid line) and chow containing 0.4% by weight DHEA (dashed line) are shown in FIG. 1B while changes in other physiological parameters are set forth in Table 1. DHEA treatment (either 0.2% or 0.4%) prevented the development of severe diabetes. Blood sugar remained within the normal range during the entire treatment period, with 0.4% by weight DHEA being somewhat more effective than 0.2% as shown in Table 1. The average blood sugar concentration in 4 mutants treated with a food diet 0.2% by weight DHEA for 12 weeks was 194±22.9 mg/dl, compared with 156±18.9 mg/dl for 11 mutants maintained on 0.4% DHEA (Table 1). DHEA treatment of normal BL/Ks mice for 16 weeks after weaning decreased average blood sugar concentration, but had little effect on plasma insulin concentration, pancreatic insulin content or the percent granulated beta cells all summarized in Table 1.

One group of older BL/Ks diabetes mutants with established, but not terminal hyperglycemia, blood sugar 340±10.5 mg/dl, was treated with 0.4% DHEA for 4 weeks. After only 2 weeks of treatment, blood sugar concentrations had normalized in all mice. The average blood sugar concentration at the time of sacrifice (4 weeks) was 155±11.2 mg/dl. Plasma insulin concentrations at sacrifice were 1857±472 µU/ml in treated mutants compared to 205±28.9 µU/ml in similarly aged untreated mutants. Pancreatic insulin content had increased to within the normal range and the percent granulated beta cells (30.5±4.9) was markedly increased, although not to normal values. Islet atrophy was not obvious in the treated mutants. The degree of islet intactness and extent of beta cell granulation, 31.3±9.6%, approached that seen in mice treated with DHEA from weaning, namely 44.2±6.2%.

The therapeutic effects of 0.4% DHEA were also studied in a group of 6 male obese (ob) mutants on the BL/Ks inbred background, data not shown. The effect in treated BL/Ks (ob/ob) mutants was similar if not identical in all parameters to those reported here for BL/Ks (db/db) mutants and in the previous publication Coleman, D. L., et al, "Therapeutic Effects of Dehydroepiandrosterone (DHEA) in Diabetes Mice", 31 *Diabetes*, 830–833 (1982). No change in the rate of weight gain or food consumption was observed. However, blood sugar concentrations were restored to normal as long as treatment continued.

In contrast to BL/Ks mutants, BL/6 mutants maintained on chow containing 0.4% DHEA gained much less weight than mutants fed chow alone. FIG. 2A shows the average growth curve for groups of 8 male BL/6 (db/db) mice fed either plain chow alone (solid line), chow containing 0.1% by weight DHEA (light dashed line) and 0.4% by weight (heavy dashed line) DHEA. The final body weight attained in the plain chow fed mutants was nearly 60 g compared to only 35 g in those mutants fed 0.4% of DHEA. Treatment with 0.1% of DHEA produced a rate of weight gain intermediate that for plain chow fed mutants and those fed 0.4% of DHEA as shown in FIG. 2A. The weights of all mice after 4 weeks of treatment with either concentration of DHEA were all significantly decreased ($P<0.01$) compared to those mutants fed plain chow alone. The weights of BL/6 diabetes mutants fed 0.1% DHEA were significantly ($P<0.01$) increased over that of mice fed 0.4% DHEA.

Studies carried out with a group of six BL/6 (ob/ob) mutants gave similar results, data not shown, except that the final body weight of obese mutants exceeded 70 g and that of mutants treated with 0.4% DHEA was 48 g. Although no determination was made of actual body composition, it was obvious at autopsy that most of the weight decrease in all BL/6 mutants fed DHEA could be attributed to a marked decrease in the accretion of adipose tissue.

Figure 2B:
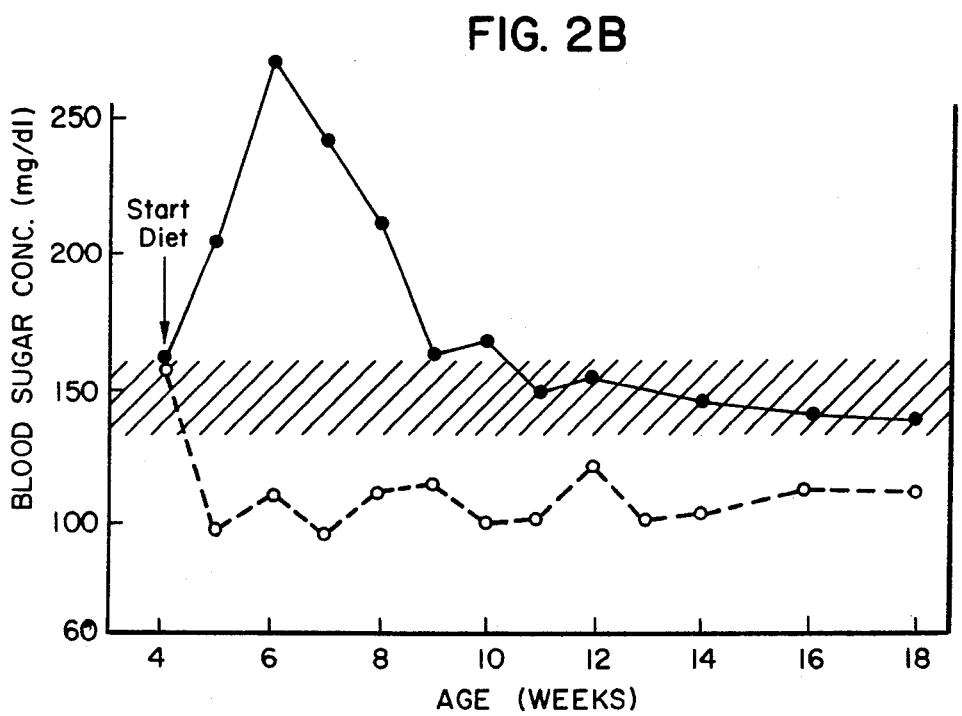
FIG. 2B as a graph showing the effect of treatment according to the invention on blood sugar concentration in BL/6 diabetes mice. The solid line connects data points for mice fed on plain chow. The dash line connects data points for mice on a food diet supplemented 0.4% by weight DHEA. The cross hatched region represents the normal range.

The effects of DHEA treatment on blood sugar concentration in BL/6 (db/db) mutants is shown in FIG. 2B and is summarized in Table 1. Mutants treated prior to the characteristic transient rise in blood sugar that typically occurs between 4–8 weeks of age as shown by the solid line of FIG. 2B failed to exhibit hyperglycemia at any time after initiation of treatment. Instead, blood sugar decreased to values below normal for the duration of the study as shown by the dashed line of FIG. 2B. The blood sugar profile of treated and untreated BL/6 (ob/ob) mutants, data not shown, was identical to that seen in BL/6 (db/db) mice. Those mutants fed only 0.1% DHEA responded equally as well as those fed 0.4% DHEA with respect to the changes in blood sugar concentrations. When treatment was initiated at 6 to 8 weeks in BL/6 diabetes or obese mutants (after mild hyperglycemia had occurred), normal glycemia was restored within a week and remained normal as long as treatment continued.

Groups of normal mice of either strain fed 0.4% DHEA from weaning always gained slightly less weight compared to mice fed plain chow alone. After a 12 week treatment period, 10 normal BL/6 male mice fed 0.4% DHEA, gained less weight (1.4 g) compared with mice fed plain chow (2.6 g). A similar reduction in weight gain was seen in BL/Ks normal mice fed DHEA. These differences were not significant. All organs appeared normal on gross examination at autopsy, except the adipose tissue, which was extremely small. Both mutant and normal BL/Ks mice fed DHEA, had normal food intakes, while BL/6 mice decreased food intake in response to DHEA treatment as shown in Table 1. Feeding of 0.4% DHEA had a greater effect on the reduction of food intake in the hyperphagic BL/6 mutants (42 percent reduction) than in normal mice (21 percent reduction).

Plasma insulin concentrations of diabetes mutants of the BL/6 genetic background fed plain chow typically increased from about 3 times normal (150 $\mu$U/ml) to over 2000 $\mu$U/ml as the disease progressed and severe insulin resistance developed (Table 1). BL/6 diabetes mice fed 0.4% of DHEA did not show as great a rise in plasma insulin concentration as those fed plain chow (1414 vs 2302 $\mu$U/ml as summarized in Table 1). In contrast BL/6 mutants fed only 0.1% of DHEA maintained the largest and most consistent increase in plasma insulin concentration ($>4000$ $\mu$U/ml).

Histological examination of the pancreas revealed large hyperactive islets with enlarged sinusoids in all BL/6 (db/db) mice regardless of diet. Pancreatic insulin content (Table 1) in plain chow fed BL/6 mutants was much higher than that seen in either plain chow or DHEA treated normal ($+/+$) BL/6 mice even though the beta cells of mutants were markedly degranulated when compared to normal mice. Feeding 0.4% DHEA to BL/6 mutants increased the extent of beta cell granulation but was without effect on pancreatic insulin content (Table 1). Feeding of DHEA at 01.% produced an intermediate effect with respect to beta cell granulation (Table 1) and rate of weight gain (FIG. 2A, light dashed line), whereas it was fully as effective as 0.4% with respect to blood sugar changes (Table 1). The inhibitory effect of DHEA on weight gain and food consumption in BL/6 mutants are in sharp contrast to the effect in BL/Ks mutants reported above, where DHEA normalized the blood sugar, but was without effect on either rate of weight gain or food consumption.

Results of DHEA Treatment During the Peri- and Postnatal Period

Initial preclinical studies involved feeding chow containing 0.4% DHEA to known heterozygous breeding pairs of each strain to assure maximal exposure of developing litters to any effects of DHEA. No pregnancies occurred when these pairs were maintained on chow containing DHEA. Litters were not obtained even when diets containing DHEA were fed to pregnant females as late as mid-term in pregnancy (12 days). Therefore, nursing dams were switched to the chow containing 0.4% DHEA 10–14 days after birth of the litter. All pups in litters from female mice fed DHEA grew more slowly than those fed plain chow alone. After weaning at 4 weeks, the presence of the db gene carried in linkage with the m gene in misty (m/m) weanlings was verified by their increased body weights irrespective of the diet fed. Blood sugar concentrations in all mutants, either BL/6 or BL/Ks remained normal as long as DHEA treatment continued. Insulin concentration, in both plasma and pancreas of mutants, was elevated (Table 2) compared to those obtained from normal littermates. Mean islet area was the same in treated BL/6 mutants whereas it was increased in BL/Ks mutants. Percent granulated beta cells was equal in mice of the BL/6 strain and decreased in mutants of the BL/Ks strain. The extent of granulation in these younger normal mice of both strains was not as great as that typical of older normal mice (approximately 60–70%). This was in sharp contrast to the severely reduced percentage seen in either BL/Ks or BL/6 (db/db) mice fed plain chow alone (Table 1). Islet atrophy typical of plain chow fed BL/Ks mutants never occurred in DHEA treated pups of either strain and correlated with the complete absence of the physiological symptoms of diabetes.

Results of Aging Studies

Figure 3:
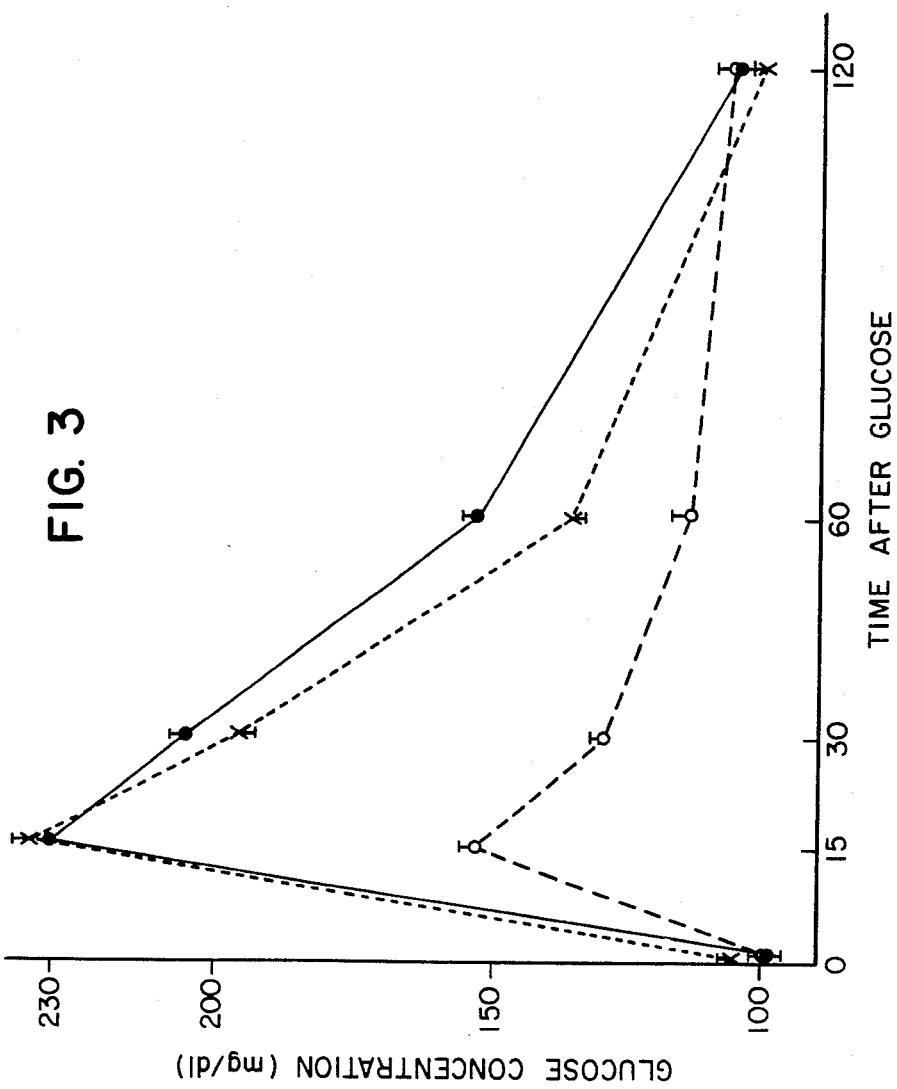
FIG. 3 is a graph showing glucose concentration derived by glucose tolerance tests administered to three groups of mice. The solid line connects data points for 2-year old BL/6 mice fed on plain chow. The dotted line connects data point x's for 1-year old BL/6 mice fed either plain chow or a food diet supplemented 0.4% by weight DHEA. The dash line connects data point 0's for 2-year old BL/6 mice fed a food diet supplemented 0.4% by weight DHEA.

There were no significant differences in plain chow fed and fasted (16 hr) blood sugar concentrations between the one year old and the two year old female BL-6 mice at the start of treatment and both groups responded normally to a glucose challenge. After 4 weeks on the DHEA containing diet, a distinct improvement in glucose handling was observed in the two year old group (dashed line) fed DHEA as shown in FIG. 3. No differences in response to glucose were seen for the younger groups, fed either plain chow or DHEA or the old group fed plain chow alone (solid line). Plasma immunoreactive insulin concentrations at sacrifice (after 8 weeks on diet) were normal in all groups (80–110 $\mu$U/ml) except for the plain chow fed 2 year old mice which had an average plasma insulin concentration of 263±3.6 $\mu$U/ml. In spite of this markedly elevated plasma insulin seen in the old untreated group, the average fed blood sugar concentration was no different than that of any of the other group (80–100 mg/dl). The plasma insulin responses, 30 minutes after glucose challenge were equivalent in both DHEA treated (53.1±5.9 $\mu$U/ml) and untreated (51.0±6.6 $\mu$U/ml) young mice whereas, insulin secretion in response to glucose challenge was enhanced in both treated (105.3±12.6 $\mu$U/ml) and untreated (122±22.2 $\mu$U/ml) older mice.

Results of Other Methods of Administration of DHEA

In one set of experiments using BL/Ks (db/db) mutants and controls, DHEA was incorporated into the diet in 2% of agar in order to obtain cubes of food which would be more convenient for studies on food consumption. The expected anti-hyperglycemic effects of DHEA treatment were not obvious after a one month trial period with the agarized, DHEA containing diet. When these mice were switched to powdered chow diet containing DHEA in finely dispersed powdered form without agar, hyperglycemia was checked and blood sugar was held at around 250 mg/dl (data not shown). However, the initial damage that occurred during the presentation of DHEA in agarized form was not completely repaired by subsequent feeding of the steroid in powdered diets. Treatment of BL/Ks diabetes mutants with DHEA by injection subcutaneously in propylene glycol (12.5 mg in 0.25 ml per day), or a lower dose in peanut oil (50 $\mu$g in 50 $\mu$l, twice a week) for two weeks was also without effect. In contrast, oral feeding of DHEA at 0.4% by weight concentration in finely dispersed powdered form mixed in the food diet had a dramatic effect on both the control of diabetes in BL/Ks mutants and the regulation of weight gain in BL/6 mutants.

Other Examples

Further examples of successful treatment of diabete and successful administration of DHEA as an oral anti-diabetic agent and oral anti-hyperglycemic agent are set forth in the article Coleman et al, "Therapeutic Effects of Dehydroepiandrosterone (DHEA) in Diabetic Mice", 31 *Diabetes*, 830–833 (September 1982).

DHEA Compounds

Similar experimental examples have been conducted with the sulfate derivative of DHEA, DHEA sulfate. DHEA sulfate has been found as effective as DHEA as an oral anti-diabetic agent and an oral anti-hyperglycemic agent for treating diabetes and enhancing beta cell function. A further advantage of DHEA sulfate is that it is soluble in water and therefore may be administered in a finely dispersed form by solution in water. When DHEA is dissolved, a ketone solvent such as acetone is used. The solution is then mixed with the food diet of the diabetic and the acetone permitted to dissolve prior to ingestion of the food diet. This procedure results in fine dispersion of the DHEA in powdered form throughout the food diet.

DHEA sulfate which is soluble in water, can be provided by mixing in the drinking water or by mixing directly with the food diet without using any solvent. It is expected and anticipated that other soluble compounds of DHEA may also be used with equal success and effectiveness such as, for example, DHEA glucuronide.

Furthermore, DHEA and its sulfate derivative have been found effective as an oral anti-diabetic agent and an oral anti-hyperglycemic agent over a wide range of dosages measured as a percent by weight of food diet and by mg DHEA compound per kg body weight of the diabetic. Thus, beneficial effects have been found at very low concentrations and at very low dosage levels, for example, as low as 120 mg per day per kg body weight. On the other hand, upper limits have been found for dosages in achieving the full expression of beneficial effects of DHEA in treating diabetes and enhancing beta cell function beyond which further increments in beneficial effect do not occur. For example, dosage levels no greater than 0.4% by weight DHEA compound in the overall food diet elicit the full beneficial effects. This corresponds to a rate of administration of, for example, up to 480 mg per kg body weight of the diabetic. Thus, incremental beneficial effects are achieved by treatment according to the present invention by dosages in the range up to 0.4% by weight of DHEA compound in the food diet and in the range of 120 mg to, for example 480 mg per day per kg body weight.

Referring to Tables I and II, certain abbreviations are used which are here clarified. The strain of mice and and genotype code are designations by The Jackson Laboratory, Bar Harbor, Maine 04609, and may be ordered directly from the mouse research colonies of this organization with further background provided in the Coleman et al article, "Diabetes-Obesity Syndromes in Mice" cited above. The percent DHEA given is the percent by weight DHEA supplement in the animal diet. The food consumption is given in grams (g) per day. Blood sugar, abbreviated B.S. is given in units of milligrams (mg) per decaliter (dl). The plasma insulin, referred to as immunoreactive insulin (IRI) is measured in micro Units per mililiter. The units (U) referred to are Standard Insulin Units. The pancreatic insulin is given in standard insulin units (U) per gram of pancreas wet weight. The granulated beta cells also referred to as $\beta$-cells are given as a percent of islet area, that is a percentage of the area of the islets of Langerhans. Table I summarizes the data from the examples for comparison of the effects of administering DHEA according to the invention on diabetic and normal BL/6 and BL/Ks mice. The data represent average values ± the standard error of the mean (SEM) for groups of male mice treated from weaning. The data for treated diabetic mice was significantly different from normal controls or untreated diabetes mutants with a confidence level $P<0.01$.

Table II summarizes data for the effects of administering DHEA according to the invention during the peri-natal and post-natal period for groups of mice of both sexes. DHEA was administered orally as a 0.4% by weight supplement of the food diet from 10 to 14 days of age until sacrifice at two months of age after 6 weeks of treatment. Again, the data for treated diabetic mice was significantly different from normal controls with a confidence level P<0.01.

Also, DHEA administered in the diet has been shown effective in forms of diabetes caused by chronic lack of insulin (insulinopenia). Mice are treated with streptozotocin (SZ), a drug that destroys the insulin producing β-cells of the islets of Langerhans and renders the mouse insulin deficient. When treated with 0.4% by weight DHEA in the food diet, for example, the fed blood sugar concentration, water consumption, and glucose tolerance tests of SZ mice have shown that the diabetic symptoms are decreased. Plasma insulin concentration of DHEA treated SZ mice were not significantly changed from that of untreated SZ mice. This suggests a potentiating effect of DHEA on the small amount of residual insulin left after the SZ treatment.

While the invention has been described with reference to successful examples in the treatment of diabetes in mice and the enhancement of pancreatic beta cell function in mice, it is intended to cover all equivalent mammalian applications and all equivalent variations and treatment within the full range of the scope of the following claims.

TABLE 1

| Strain | Genotype (n) | % DHEA | Food Consumption (g) | B.S. (mg/dl) | Plasma IRI (μU/ml) | Pancreatic insulin (U/g) | Granulated beta cells (%) |
|---|---|---|---|---|---|---|---|
| BL/Ks | +/+ (6) | 0.0 | 4.04 ± 0.20 | 131 ± 2.04 | 42.4 ± 1.96 | 3.84 ± 0.63 | 68.8 ± 7.10 |
|  | +/+ (3) | 0.4 | 3.95 ± 0.18 | 101 ± 1.42 | 51.4 ± 3.34 | 3.89 ± 0.13 | 79.4 ± 5.80 |
|  | db/db (11) | 0.0 | 4.19 ± 0.16 | >450 | 205 ± 28.9 | 1.06 ± 0.25 | 4.06 ± 1.08 |
|  | db/db (11) | 0.4 | 6.21 ± 0.11 | 156 ± 18.9 | 2374 ± 1883 | 10.4 ± 0.08 | 44.2 ± 6.18 |
|  | db/db (4) | 0.2 | n.d. | 194 ± 22.9 | 1310 ± 241.9 | 6.5 ± 3.38 | 28.0 ± 14.40 |
| BL/6 | +/+ (6) | 0.0 | 3.82 ± 0.15 | 140 ± 4.00 | 37.3 ± 5.42 | 2.67 ± 0.17 | 76.3 ± 2.35 |
|  | +/+ (5) | 0.4 | 3.03 ± 0.13 | 118 ± 3.51 | 37.4 ± 8.92 | 2.29 ± 0.12 | 70.3 ± 3.42 |
|  | db/db (16) | 0.0 | 4.82 ± 0.17 | 140 ± 15.00 | 2302 ± 453.70 | 8.50 ± 1.89 | 14.4 ± 4.37 |
|  | db/db (10) | 0.4 | 2.78 ± 0.18 | 111 ± 9.23 | 1414 ± 344.60 | 8.97 ± 1.48 | 49.9 ± 6.75 |
|  | db/db (6) | 0.1 | n.d. | 126 ± 12.70 | >4000 | 12.0 ± 2.79 | 26.4 ± 2.84 |

TABLE 2

| Genotype (No.) | Plasma IRI μU/ml | Pancreatic insulin U/g | Granulated beta cells % | Mean islet area μm² |
|---|---|---|---|---|
| BL/6 +/? (6) | 84.3 ± 14.2 | 4.74 ± 0.59 | 63.3 ± 4.42 | 8282 ± 1098 |
| BL/6 mdb/mdb (6) | 405 ± 107.3 | 6.79 ± 1.69 | 62.4 ± 5.18 | 8804 ± 540 |
| BL/Ks +/? (9) | 81 ± 9.63 | 3.74 ± 0.38 | 75.2 ± 1.35 | 10809 ± 1103 |
| BL/Ks mdb/mdb (6) | 477 ± 122.5 | 16.6 ± 4.92 | 53.4 ± 6.13 | 24683   6123 |

We claim:

1. A method for treating diabetes and enhancing the pancreatic beta cell function of diabetics comprising administering a DHEA compound selected from the group consisting of dehydroepiandrosterone (DHEA), DHEA sulfate, and soluble compounds of DHEA.

2. The method of claim 1 comprising orally administering said DHEA compound in finely dispersed form.

3. The method of claim 2 further comprising the step of preparing said DHEA compound by dissolving the DHEA compound in a DHEA compound solvent thereby forming a DHEA compound solution.

4. The method of claim 3 further comprising the step of mixing the DHEA compound solution with the food diet of the diabetic.

5. The method of claim 4 further comprising the step of evaporating the DHEA compound solvent from the food diet prior to ingestion by the diabetic.

6. The method of claim 5 further comprising the step of orally administering the DHEA compound at a dosage in the range of up to 0.4% by weight of the food diet of the diabetic.

7. The method of claim 6 further comprising adjusting the dosage of the DHEA compound for administering the DHEA compound at a rate in the range of 120 mg to 480 mg per day per kg body weight of the diabetic.

8. The method of claim 1 wherein said soluble DHEA compounds comprise DHEA glucuronide.

9. The method of claim 2 wherein the DHEA compound comprises DHEA sulfate administered by mixing the DHEA sulfate in the drinking water of the diabetic.

10. A method for treating diabetes and for enhancing the pancreatic beta cell function of a diabetic comprising orally administering dehydroepiandrosterone (DHEA) to the diabetic.

11. The method of claim 10 comprising orally administering DHEA in a finely dispersed powdered form.

12. The method of claim 11 comprising orally administering DHEA in a finely dispersed powdered form mixed with the diet of the diabetic.

13. The method claim 12 further comprising the step of preparing the DHEA in finely dispersed powdered form by dissolving the DHEA in a DHEA solvent to form a DHEA solution, mixing the solution with the food diet of the diabetic, and substantially completely evaporating the solvent from the food diet of the diabetic before ingestion of the mixture of finely dispersed powdered DHEA and food diet.

14. The method of claim 13 comprising orally administering DHEA in dosages in a range of up to 0.4% by weight of the food diet of the diabetic.

15. The method of claim 12 comprising orally administering DHEA in the dosage range of 0.1% to 0.4% by weight of the food diet of the diabetic.

16. The method of claim 13 comprising dissolving the DHEA in acetone.

17. The method of claim 10 comprising orally administering DHEA in dosages in the range of 120 mg to 480 mg per kg of body weight of the diabetic per day.

18. A method for treating diabetes and for enhancing the pancreatic beta cell function of diabetics comprising:

preparing a soluble dehydroepiandrosterone (DHEA) compound in finely dispersed form by dissolving the DHEA compound in a DHEA compound solvent to provide a DHEA compound solution:

mixing the DHEA compound solution in the food diet of the diabetic in an amount in the dosage range of up to 0.4% by weight of the food diet of the diabetic:

substantially completely evaporating the DHEA compound solvent from the food diet after mixing and before ingestion of the food diet by the diabetic:

and adjusting the dosage in the food diet of the diabetic for administering DHEA compound in the range of 120 mg to 480 mg per day per kg body weight of the diabetic.

19. The method of claim 18 comprising continuing said treatment indefinitely.

20. The method of claim 18 comprising commencing said treatment before the blood sugar level of the diabetic exceeds a concentration of 350 mg/dl.

* * * * *

UNITED STATES PATENT AND TRADEMARK OFFICE
CERTIFICATE OF CORRECTION

PATENT NO. : 4,518,595
DATED : May 21, 1985
INVENTOR(S) : Douglas L. Coleman et al.

It is certified that error appears in the above-identified patent and that said Letters Patent is hereby corrected as shown below:

On the title page, Item [73] Assignee: should read:

-- The Jackson Laboratory, Bar Harbor, Me. and Progenics, Inc., New York, NY, a part interest each --.

Signed and Sealed this

Twenty-fourth Day of September 1985

[SEAL]

Attest:

Attesting Officer

DONALD J. QUIGG

Commissioner of Patents and Trademarks—Designate